United States Patent [19]
Bahrmann et al.

[11] Patent Number: 6,103,908
[45] Date of Patent: Aug. 15, 2000

[54] NONAQUEOUS IONIC LIGAND LIQUIDS, PROCESS FOR PREPARING THEM AND THEIR USE AS CATALYST CONSTITUENTS

[75] Inventors: Helmut Bahrmann, Hamminkeln; Markus Schulte, Oberhausen, both of Germany

[73] Assignee: Celanese GmbH, Germany

[21] Appl. No.: 09/212,822

[22] Filed: Dec. 16, 1998

[30] Foreign Application Priority Data

Dec. 22, 1997 [DE] Germany .............................. 197 56 945

[51] Int. Cl.$^7$ ................................. C07F 9/50; C07F 9/54
[52] U.S. Cl. ....................... 546/347; 546/192; 548/335.1; 548/373.1; 562/35; 568/909
[58] Field of Search ................................. 562/35; 546/347

[56] References Cited

U.S. PATENT DOCUMENTS

| | | | |
|---|---|---|---|
| 4,248,802 | 2/1981 | Kuntz et al. | 568/454 |
| 4,710,321 | 12/1987 | Bahrmann et al. | 260/501.15 |
| 4,716,250 | 12/1987 | Abatjoglou et al. | 568/454 |

FOREIGN PATENT DOCUMENTS

| | | |
|---|---|---|
| 0163233 | 12/1985 | European Pat. Off. . |
| 0254937 | 2/1988 | European Pat. Off. . |
| 0302375 | 2/1989 | European Pat. Off. . |
| 2314910 | 1/1977 | France . |
| 0776880 | 6/1997 | France . |

*Primary Examiner*—Bernard Dentz
*Attorney, Agent, or Firm*—Bierman, Muserlian and Lucas

[57] ABSTRACT

Nonaqueous ionic ligand liquids of the formula $(Q^{\oplus})_a A^{a-}$, where $Q^{\oplus}$ is a singly charged quaternary ammonium and/or phosphonium cation or the equivalent of a multiply charged ammonium and/or phosphonium cation and $A^{a-}$ is a sulfonated triarylphosphine, a process for preparing them and their use as catalyst constituents.

20 Claims, No Drawings

NONAQUEOUS IONIC LIGAND LIQUIDS, PROCESS FOR PREPARING THEM AND THEIR USE AS CATALYST CONSTITUENTS

The present invention relates to nonaqueous ionic ligand liquids of the formula $(Q^{\oplus})_a\, A^{a-}$, where $Q^{\oplus}$ is a singly charged quaternary ammonium and/or phosphonium cation or the equivalent of a multiply charged ammonium and/or phosphonium cation and $A^{a-}$ is a sulfonated triarylphosphine, a process for preparing them and their use as catalyst constituents.

STATE OF THE ART

Many economically important processes such as the hydroformylation reaction and the hydrogenation or dimerization of olefins are carried out in the presence of a catalytically active transition metal compound. The catalytically active transition metal compounds comprise, for example, metals of group VIII of the Periodic Table of the Elements as transition metal and, for example, carbon monoxide and tertiary arylphosphines as ligands.

Such processes can be carried out in a single organic phase where the catalyst, for example a rhodium/triphenylphosphine complex, is present in dissolved form in the organic reaction mixture.

However, the separation of the reaction products and the recovery of the catalysts homogeneously dissolved in the reaction product present problems in this process. In general, the reaction product is distilled from the reaction mixture, but problems can occur in practice if the reaction products formed are thermally sensitive. In addition, the thermal stressing of the material being distilled can lead to considerable losses of product as a result of by-product formation and to losses of catalyst as a result of decomposition of the catalytically active complexes.

These deficiencies can be avoided if such processes are carried out in a two-phase system. An example of a process carried out in a two-phase system in the presence of a catalytically active transition metal compound is described in DE-C 26 27 354. This process is distinguished by the presence of an organic phase comprising the starting olefins and the reaction product and an aqueous phase in which the catalyst is dissolved. Catalysts used are water-soluble rhodium complexes which contain water-soluble phosphines as ligands. The phosphines include, in particular, triarylphosphines, trialkylphosphines and arylated or alkylated diphosphines whose organic radicals are substituted by sulfonic acid groups or carboxyl groups. Their preparation is known, for example, from DE-C 26 27 354.

The use of an aqueous catalyst-containing phase in other chemical processes, e.g. in hydrogenation or hydrodimerization is known from Applied Homogeneous Catalysts in organometallic Compounds, Volume 2, 1996 VCH Publishers, New York and Angew. Chem. Int. Ed. Engl. 1993, 32, 1524–1544.

Successful implementation of the two-phase process using an aqueous catalyst solution requires not only sufficient solubility of the substrate to be reacted in the aqueous phase but also sufficient stability of the catalyst complex toward water. For this reason, water-sensitive complexes cannot be reacted in the two-phase process in the presence of an aqueous catalyst-containing phase.

To overcome this disadvantage without giving up the advantage of the two-phase process, the use of nonaqueous ionic liquids as solvents for catalyst complexes is proposed.

According to CHEMTECH, September 1995, pages 26 to 30, nonaqueous ionic compositions which are liquid at room temperature, e.g. a mixture of 1,3-dialkylimidazolium chloride, preferably 1-n-butyl-3-methylimidazolium chloride, and aluminum chloride and/or ethylaluminum dichloride, can be used as nonaqueous solvents for the catalyst complex. In the prior art, the 1-n-butyl-3-methylimidazolium cation is abbreviated as $BMI^{\oplus}$. Examples of reactions which have been successfully carried out in this way are olefin dimerization in the presence of nickel complexes, e.g. the dimerization of propene to give isomeric hexenes or the dimerization of butene to give isooctenes. The reaction product forms the upper phase while the catalyst-containing nonaqueous ionic liquid forms the lower phase and can be separated off by simple phase separation. The catalyst-containing nonaqueous ionic liquid can be returned to the process.

It is known from Am. Chem. Soc., Div. Pet. Chem (1992), 37, pages 780 to 785, that a nonaqueous ionic liquid comprising 1-n-butyl-3-methylimidazolium chloride and aluminum chloride can serve as a solvent in which, after addition of ethylaluminum dichloride and $NiCl_2(PR_3)_2$ where R is isopropyl, the dimerization of propene is carried out.

The use of low-melting phosphonium salts, e.g. tetrabutylphosphonium bromide, as solvent in hydroformylation reactions is disclosed in Journal of Molecular Catalysis, Vol. 47 (1988), pages 99–116. According to this, the hydroformylation of olefins, e.g. 1-octene, using ruthenium carbonyl complexes in the presence of nitrogen- or phosphorus-containing ligands, e.g. 2,2'-dipyridyl or 1,2-bis (diphenylphosphino)ethane, at temperatures of from 120 to 180° C. gives a mixture of n-nonanol and n-nonanal. In this process, n-nonanol is obtained in a proportion of up to 69% by weight, based on the reaction mixture so that a complicated distillation step is required to isolate the desired n-nonanal.

EP-A-0 776 880 discloses hydroformylation of olefins in the presence of quaternary ammonium and/or phosphonium salts as solvent, with preference being given to using the 1-n-butyl-3-methylimidazolium cation

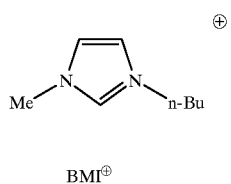

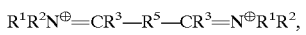

$BMI^{\oplus}$ as cation. However, use is also made of salts of quaternary diamines in which the cation has the formula:

$$R^1R^2N^{\oplus}=CR^3-R^5-CR^3=N^{\oplus}R^1R^2,$$

where $R^1$, $R^2$, $R^3$ are individually each hydrogen or a hydrocarbon of 1 to 12 carbon atoms and $R^5$ is alkylene, e.g. methylene, ethylene or propylene, or phenylene. Suitable anions are, for example, hexafluorophosphate, hexafluoroantimonate, tetrachloroaluminate and tetrafluoroborate. These quaternary ammonium and/or phosphonium salts are liquid at below 90° C., preferably below 85° C. and more preferably below 50° C. The hydroformylation catalyst is present as a solution in them.

The hydroformylation catalyst comprises cobalt, rhodium, iridium, ruthenium, palladium or platinum as active metal and a tertiary phosphine or tertiary sulfonated phosphine, a tertiary arsine, tertiary stibine or a phosphite as ligand. According to EP-A-0 776 880, the molar ratio of ligand to metal is 9.5.

Examples of suitable compounds which contain the active metals and from which the hydroformylation catalyst is formed under the reaction conditions are dicarbonylrhodium acetylacetonate or rhodium carbonyl $Rh_6(CO)_{16}$. Particular preference is given to carrying out the hydroformylation reaction at from 30 to 90° C.

Angew. Chem. 1995, Vol 107, No. 23/24, pages 2941 to 2943, also discloses the use of 1,3-dialkylimidazolium salts which are liquid at room temperature as catalyst-containing solvent which is immiscible with the organic reaction mixture for carrying out hydroformylation reactions. Here, dicarbonylrhodium acetylacetonate is added as catalyst precursor to a solution of triphenylphosphine in $BMI^{\oplus}$ hexafluorophosphate, with the molar ratio of phosphorus (III) to rhodium being able to vary from 3 to 10. The catalyst is performed by addition of synthesis gas containing hydrogen and carbon monoxide in a volume ration of 1:1. After addition of 1-n-pentene, the reaction is carried out using synthesis gas of the same composition at a temperature of 80° C. In this case too, the organic product phase can be separated from the catalyst-containing nonaqueous ionic liquid in a simple manner by decantation.

The known processes all use a nonaqueous ionic liquid as solvent for the catalytically active metal complex. The use of the nonaqueous ionic liquid introduces additional anions which do not serve as ligands, e.g. hexafluoroantimonate or hexafluorophosphate, into the process. Furthermore, the prior art known from Angew. Chem. 1995, Vol. 107, No. 23/24, pages 2941 to 2943, and EP-A-0 776 880 teaches a molar ratio of ligand/metal, e.g. a molar ratio of phosphorus to rhodium, of from 3 to 10. Higher molar ratios of ligand to metal, e.g. of phosphorous to rhodium, are not disclosed in the prior art. A higher molar ratio of ligand to metal presumably leads to precipitation or an increased loss of the ligand from the nonaqueous ionic liquid disclosed.

A disadvantage of the known processes is the loss of the catalytically active metal from the nonaqueous ionic liquid to the organic phase. According to the prior art, this disadvantage can be overcome by using charged ligands, e.g. monosulfonated or trisulfonated triphenylphosphine, in place of neutral ligands, e.g. triphenylphosphine, since it is to be expected that charged ligands will increase the solubility of the catalytically active metal compounds in the nonaqueous ionic liquid. Even if it were possible to reduce the loss of the catalytically active metal in this way by use of charged ligands, the yields of desired product, e.g. aldehydes, are decreased to only 16–33% (Angew. Chem. 1995, 107, No. 23/24, pages 2941 to 2943, EP-A-0 776 880).

OBJECTS OF THE INVENTION

It is an object of the invention to provide a nonaqueous ionic liquid which is immiscible with the organic phase and is suitable for preparing a catalyst which allows the conversion of the starting materials into the desired products simply and economically in high yields.

This and other objects and advantages of the invention will become obvious from the following detail description.

THE INVENTION

This object is achieved by a nonaqueous ionic ligand liquid of the formula $(Q^{\oplus})a\ A^{a-}$, wherein $Q^{\oplus}$ is a singly charged quaternary ammonium and/or phosphonium cation or the equivalent of a multiply charged ammonium and/or phosphonium cation and $A^{a-}$ is a triarylphosphine of the formulae:

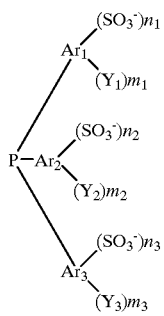

where $Ar_1$, $Ar_2$ and $Ar_3$ are individually aryl of 6 to 14 carbon atoms, the substituents $Y_1$, $Y_2$ and $Y_3$ are individually selected from the group consisting of alkyl and alkoxy of 1 to 4 carbon atoms, chlorine, bromine, hydroxyl, cyano, nitro and amino groups of the formula $NR^1R^2$, where $R^1$ and $R^2$ are individually hydrogen or alkyl of 1 to 4 carbon atoms, m1, m2, and m3 are individually integers from 0 to 5, n1, n2 and n3 are individually integers from 0 to 3, where at least one of $n_1$, $n_2$ and $n_3$ is equal to or greater than 1, and a is $n_1+n_2+n_3$, and amines and/or phosphines derived from $Q^{\oplus}$ are present in an excess of up to 5 equivalents over the stoichiometrically required amount for the formation of $(Q^{\oplus})a\ A^{a-}$ or alkali metal or alkaline earth metal salts of the triarylphosphines $A^{a-}$ are present in an excess of up to 5 equivalents over the stoichiometrically required amount for the formation of $(Q^{\oplus})\ a\ A^{a-}$.

It has surprisingly been found that the nonaqueous ionic ligand liquids of the invention are, after addition of at least one catalytically active transition metal and/or its compound, suitable as a catalyst system in chemical processes catalyzed by transition metals.

It has been found that the use of the nonaqueous ionic ligand liquids of the invention in processes catalyzed by transition metals allows the use of a high molar ratio of ligand to transition metal, e.g. a molar ratio of phosphorus to rhodium, of more than 100. A high excess of ligand, e.g. of sulfonated triphenylphosphine, has a stabilizing effect on the catalytically active metal complexes during the catalysis cycle.

In the following, "catalyst system" means the nonaqueous ionic ligand liquid together with the catalytically active transition metal compounds.

Stabilized catalyst systems have a low rate of loss of catalytically active transition metal and allow frequent recycling of the used catalyst system to be processed without a drop in activity and selectivity being observed. Stabilized catalyst systems therefore give higher yields of desired product and have longer catalyst operating lives than unstabilized catalyst systems.

When using nonaqueous ionic liquids and nonaqueous ionic ligand liquids, the lengthening of the catalyst operating lives, as is known to be able to be achieved by stabilized catalyst systems, is of particular importance since the exhausted catalyst phase after discharge from the process represents a substantial salt burden which has to be dealt with by costly reprocessing and/or disposal. Exhaustion of the catalyst system is indicated by a drop in the catalyst activity and selectivity to a level below that which is economically acceptable.

The decreases in activity and selectivity are caused, for example, by the accumulation of catalyst degradation products. If processes catalyzed by transition metals are carried out in nonaqueous ionic liquids, excessively rapid exhaustion of the catalyst system which requires the subsequent discharge from the process is therefore a disadvantage. The nonaqueous ionic ligand liquids of the invention make it possible to employ advantageous, high molar ratios of ligand to metal which lead to stabilized catalyst systems having long catalyst operating lives.

It may be assumed that the catalytically active transition metal compounds are formed under the respective reaction conditions from the transition metal, which is added either in metallic form or as a customary transition metal compound, and the nonaqueous ionic ligand liquid. The nonaqueous ionic ligand liquid and the catalytically active transition metal compound form the catalyst system.

The nonaqueous ionic ligand liquids of the invention can comprise amines and/or phosphines derived from $Q^\oplus$ in an excess over the stoichiometrically required amount for the formation of $(Q^\oplus)_a A^{a-}$ or alkali metal and/or alkaline earth metal salts of the triarylphosphines $A^{a-}$ in an excess over the stoichiometrically required amount for the formation of $(Q^\oplus)_a A^{a-}$. In general, the excess over the stoichiometrically required amount for the formation of $(Q^\oplus)_a A^{a-}$ is up to 5 equivalents of amines and/or phosphines derived from $Q^\oplus$ or of alkali metal and/or alkaline earth metal salts of the triarylphosphines $A^{a-}$. This excess is preferably from 0 to 1 equivalent.

Cations $Q^\oplus$ which can be used for preparing the nonaqueous ionic ligand liquids of the invention are quaternary ammonium and/or phosphonium cations of the formula $^\oplus NR^1R^2R^3R^4$ or $^\oplus PR^1R^2R^3R^4$ or the formula $R^1R^2N^\oplus=CR^3R^4$ or $R^1R^2P^\oplus=CR^3R^4$, where $R^1$, $R^2$, $R^3$ and $R^4$ are individually each hydrogen, with the exception of $NH_4^+$, or a hydrocarbon of 1 to 20 carbon atoms, for example alkyl, alkenyl, cycloalkyl, alkylaryl, aryl or aralkyl.

Other cations suitable for preparing the nonaqueous ionic ligand liquids of the invention are heterocyclic ammonium and/or phosphonium cations of the formulae:

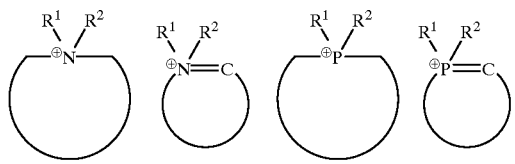

which have 1, 2 or 3 nitrogen and/or phosphorus atoms in the ring. The heterocycles have from 4 to 10, preferably 5 or 6, ring atoms. $R^1$ and $R^2$ are as defined above.

Further suitable cations are quaternary ammonium and phosphonium cations of the formulae:

$R^1R^{2\oplus}N=CR^3-X-R^3C=^\oplus NR^1R^2$ $R^1R^{2\oplus}P=CR^3-X-R^3C=PR^1R^2$ where $R^1$, $R^2$ and $R^3$ are individually as defined above and X is alkylene or phenylene. $R^1$, $R^2$, $R^3$ are, for example, hydrogen or methyl, ethyl, propyl, isopropyl, butyl, secondary butyl, tertiary butyl, amyl, methylene, ethylidene, phenyl or benzyl. X is 1,2-phenylene, 1,3-phenylene, 1,4-phenylene or alkylene, for example methylene, ethylene, propylene or 1,4-butylene.

Other cations $Q^\oplus$ which are suitable for preparing the nonaqueous ionic ligand liquid of the invention are N-butylpyridinium, N-ethylpyridinium, 1-n-butyl-3-methylimidazolium, diethylpyrazolium, 1-ethyl-3-methylimidazolium, pyridinium, triethylphenylammonium and tetrabutylphosphonium cations.

Further cations $Q^\oplus$ which are suitable for preparing the nonaqueous ionic ligand liquids of the invention are quaternary ammonium and/or phosphonium cations of the formulae:

 (quaternary diamines)

 (Gruaternary diphosphines)

where $R^1$, $R^2$, $R^3$, $R^4$, $R^5$ and $R^6$ are individually selected from the group consisting of hydrogen and hydrocarbon of 1 to 20 carbon atoms, for example alkyl, alkenyl, cycloalkyl, alkylaryl, aryl or aralkyl, and X is 1,2-phenylene, 1,3-phenylene, 1,4-phenylene or alkylene $-(CHR^7)_b$, where $R^7$ is hydrogen or hydrocarbon of 1 to 5 carbon atoms, for example methyl, ethyl, n-propyl, i-propyl, n-butyl, i-butyl or t-butyl, and b is an integer from 1 to 8. Examples of X are methylene, ethylene, propylene, butylene and 1,4-phenylene.

The quaternary ammonium cations of the formula $R^1R^2R^3N^\oplus-(X)-N^\oplus R^4R^5R^6$ are hereinafter referred to as quaternary diamines.

Quaternary diamines which are suitable for preparing the nonaqueous ionic ligand liquids of the invention include those quaternary diamines of the formula $R^1R^2R^3N^\oplus-(CHR^7)_b N^\oplus R^4R^5R^6$ in which $R^1$, $R^2$, $R^3$, $R^4$, $R^5$ and $R^6$ are individually selected from the group consisting of hydrogen, n-butyl, n-pentyl, n-hexyl, n-heptyl, i-heptyl, n-octyl, i-octyl, n-nonyl, i-nonyl, n-decyl, i-decyl, n-undecyl, i-undecyl, n-dodecyl or i-dodecyl, $R^7$ is hydrogen, methyl or ethyl and b is 2, 3, 4, 5 or 6.

Quaternary diamines which are particularly suitable for preparing the nonaqueous ionic ligand liquids of the invention are those derived from 1-amino-3-dialkylaminopropanes of the formula:

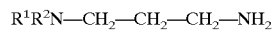

where $R^1$ and $R^2$ are individually alkyl of 4 to 20 carbon atoms, such as n-butyl, n-pentyl, n-hexyl, n-heptyl, i-heptyl, n-octyl, i-octyl, i-nonyl, n-nonyl, n-decyl, i-decyl, n-undecyl, i-undecyl, n-dodecyl or i-dodecyl.

The nonaqueous ionic ligand liquids of the invention can be prepared particularly advantageously if 1-amino-3-(di-n-heptyl)aminopropane, 1-amino-3-(di-i-heptyl)-aminopropane, 1-amino-3-(di-n-octyl)aminopropane, 1-amino-3-(di-i-octyl)aminopropane, 1-amino-3-(di-n-nonyl)aminopropane, 1-amino-3-(di-i-nonyl)aminopropane, 1-amino-3-(di-n-undecyl)aminopropane, 1-amino-3-(di-i-undecyl)aminopropane, 1-amino-3-(di-n-dodecyl)-aminopropane or 1-amino-3-(di-i-dodecyl)aminopropane are used for preparing the quaternary diamines.

The 1-amino-3-dialkylaminopropanes are prepared by reacting N,N-(dialkyl)amines of the formula:

where $R^1$ and $R^2$ are individually alkyl of 4 to 20 carbon atoms, particularly n-butyl, n-pentyl, n-hexyl, n-heptyl, i-heptyl, n-octyl, i-octyl, i-nonyl, n-nonyl, n-decyl, i-decyl, n-undecyl, i-undecyl, n-dodecyl or i-dodecyl groups, with acrylonitrile by known methods (cf. Ullmanns Encyclopedia of Industrial Chemistry, Vol. A2, 1985). As further diamines derived from $Q^\oplus$, it is possible to use tricyclodecanediamine and N,N'-dimethylethyl-tricyclodecane diamine.

To prepare the nonaqueous ionic ligand liquid of the invention, it is possible to use the sulfonated triarylphosphines of the formula:

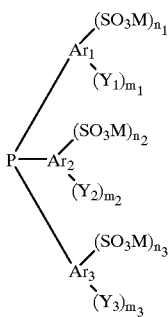

in which $Ar_1$, $Ar_2$ and $Ar_3$ are individually aryl of 6 to 14 carbon atoms, $Y_1$, $Y_2$ and $Y_3$ are individually selected from the group consisting of alkyl and alkoxy of 1 to 4 carbon atoms, chlorine, bromine, hydroxyl, cyano, nitro and $NR^1R^2$, where the substituents $R^1$ and $R^2$ are individually hydrogen or alkyl of 1 to 4 carbon atoms, M is lithium, sodium, potassium, magnesium, calcium or barium, $m_1$, $m_2$ and $m_3$ are individually integers from 0 to 5, $n_1$, $n_2$ and $n_3$ are individually integers from 0 to 3, where at least one of $n_1$, $n_2$ and $n_3$ is equal to or greater than 1. Their preparation is known from DE-C 26 27 354.

Preferred triarylphosphines are those in which the groups $Ar_1$, $Ar_2$, $Ar_3$ are phenyl, $Y_1$, $Y_2$ and $Y_3$ are individually methyl, ethyl, methoxy or ethoxy and/or chlorine, and the cationic entities M are inorganic cations of sodium, potassium, calcium or barium. Particularly suitable triarylphosphines are those in which $Ar_1$, $Ar_2$, $Ar_3$ are phenyl, $m_1$, $m_2$, $m_3$ are 0, $n_1$, $n_2$ and $n_3$ are 0 or 1 and the sum of $n_1+n_2+n_3$ is from 1 to 3 and the sulfonated groups are in the meta position.

Aqueous solutions of sodium, potassium, calcium or barium salts of (sulfophenyl)diphenylphosphine, di(sulfophenyl)phenyl-phosphine or tri(sulfophenyl)phosphine are particularly suitable. It is also possible to use mixtures of these aqueous solutions. However, it is advantageous to use a single aqueous salt solution of one of the above-mentioned alkali metals and alkaline earth metals, particularly an aqueous sodium or potassium salt solution. This solution may also contain a mixture of (sulfophenyl)diphenylphosphine, di(sulfophenyl)phenylphosphine and tri(sulfophenyl)-phosphine.

A mixture suitable for preparing the nonaqueous ionic ligand liquids of the invention is obtained in the sulfonation of triphenylphosphine, as known, for example, from DE-A 26 27 354.

If tricyclodecanediamine or N,N'-dimethyl-tricyclodecanediame is used as the amine for preparing the nonaqueous ionic ligand liquids, a mixture having as high as possible a content of di(sulfophenyl)phenylphosphine should be used.

The nonaqueous ionic ligand liquid of the invention is prepared by protonating and/or alkylating the amine and/or phosphine used to form the singly or multiply charged cation $Q^\oplus$ by use of acids and/or alkylating agents in the presence of an aqueous solution of the alkali metal and/or alkaline earth metal salts of the triarylphosphines $A^{a-}$.

Acids which can be used are hydrogen acids, e.g. tetrafluoroboric acid or hexafluorophosphoric acid, or oxo acids, e.g. phosphoric acid, sulfuric acid, nitric acid, phosphonic acids of 1 to 20 carbon atoms or sulfonic acids of 1 to 20 carbon atoms. Preference is given to using an aqueous sulfuric acid or phosphoric acid solution which generally has a concentration of from 10 to 30% by weight.

Alkylating agents used are, for example, monoalkyl or dialkyl sulfates or dialkyl carbonates of 1 to 41 carbon atoms or alkyl halides of 1 to 10 carbon atoms.

The amount of acid and/or alkylating agent is generally in a range from 0.9 to 2.0 equivalents per equivalent of the amines and/or phosphines used. Preference is given to using from 1 to 1.5 equivalents per equivalent of the amines and/or phosphines used. If an acid is added, the pH after addition of the acid is from 2 to 5, preferably from 3 to 4.

The amount of the amines and/or phosphines derived from $Q^\oplus$ and the alkali metal and/or alkaline earth metal salts of the triarylphosphines $A^{a-}$ must be such that an excess over the stoichiometrically required amount for the formation of $(Q^\oplus)_a A^{a-}$ can be used. In general, this excess is from 0 to 5 equivalents of the amines and/or phosphines derived from $Q^\oplus$ or the alkali metal and/or alkaline earth metal salts of the triarylphosphines $A^{a-}$. This excess is preferably from 0 to 1 equivalent.

The respective amine and/or phosphine is generally used as a 20–70% strength by weight solution, preferably a 40–60% strength by weight solution, in an organic solvent.

Suitable organic solvents are aliphatic or aromatic hydrocarbons such as benzene, toluene, o-xylene, m-xylene, p-xylene, mesitylene, n-heptane, n-octane or cyclohexane ethers such as 1,4-dioxane or tetrahydrofuran. Preference is given to using toluene or cyclohexane as solvent.

The addition of the acid and/or the alkylating agent to the mixture of the aqueous solution of the alkali metal and/or alkaline earth metal salts of the triarylphosphines $A^{a-}$ and the organic solution of the amine and/or phosphine is carried out at a temperature of from 0 to 60° C., preferably from 20 to 30° C. The duration of the addition is generally from 0.5 to 3 hours, preferably from 1 to 2 hours.

Three phases are obtained, viz. a lower aqueous phase in which the alkali metal and/or alkaline earth metal salt liberated from the triarylphosphines used is present in dissolved form, a middle phase which represents the nonaqueous ionic ligand liquid and an upper phase which comprises the organic solvent and possibly amine and/or phosphine. The desired nonaqueous ionic ligand liquid can be isolated by simple phase separation.

To form the three phases, it can be advantageous to add an organic solvent again after the addition of the acid and/or the alkylating agent; preference is given to using the same organic solvent as was used for dissolving the amine and/or phosphine. The amount of additional organic solvent necessary to obtain separation into three phases can be determined by simple preliminary tests.

In a further embodiment, an aqueous solution of the alkali metal and/or alkaline earth metal salts of the triarylphosphines $A^{a-}$ can first be treated with an acid and/or an alkylating agent and, subsequently, an organic solution of amine and/or phosphine can be added. It is also possible to mix the amine and/or phosphine to be protonated and/or alkylated with the acid and/or the alkylating agent first and to add an aqueous solution of the alkali metal and/or alkaline earth metal salts of the triarylphosphines $A^{a-}$ subsequently.

The nonaqueous ionic ligand liquids of the invention are not miscible with the organic phase and can, after addition of a transition metal or a transition metal compound, be used as a catalyst system in chemical processes catalyzed by transition metals. An example of a chemical process catalyzed by transition metals is hydroformylation.

Catalytically active transition metals include the elements of groups VI, VII and VIII of the Periodic Table of the Elements. Particularly suitable transition metals are cobalt, rhodium, iridium, ruthenium, palladium and platinum.

These transition metals are used either in elemental form as metal or as compounds. In metallic form, they are used either as finely divided particles or deposited in a thin layer on a support such as activated carbon, calcium carbonate, aluminum silicate or alumina.

Suitable compounds of these transition metals are, for example, the metal oxides or the salts of inorganic hydrogen and oxo acids, e.g. nitrates, sulfates of phosphates, carbonyl compounds, complexes such as cyclooctadienyl complexes, cyclopentadienyl complexes or acetylacetonato complexes or salts of aliphatic monocarboxylic and polycarboxylic acids, e.g. 2-ethylhexanoates, acetates, propionates, butyrates, salts of the valeric acids, malonates or oxalates. Preference is given to use of 2-ethylhexanoates.

The catalyst system can first be formed in a preforming step and then added to the reaction mixture as a preformed system. Here, the desired amount of the transition metal, either in metallic form or as a compound, is added to the nonaqueous ionic ligand liquid and the reaction mixture is treated with the agents to be reacted, for example, hydrogen and carbon monoxide. It may be assumed that the catalyst system is formed from the added transition metal and/or its compound and the nonaqueous ionic ligand liquid in the presence of the agents and, on subsequent addition of the starting material to be reacted with the agents, for example the olefin or the olefinically unsaturated compound, allows the conversion of the added starting material into the desired products, for example the aldehydes.

The catalyst system can equally successfully be prepared under reaction conditions, i.e. in the presence of the starting material to be reacted, for example the olefin or the olefinically unsaturated compound.

The reaction can be carried out either batchwise or continuously. After the reaction is complete, the desired product is present in an organic upper phase and the catalyst system is present as a lower phase, and the two phases can be separated from one another by simple phase separation. After phase separation, the catalyst system can be returned to the reaction process.

The use of the nonaqueous ionic ligand liquids of the invention in chemical processes catalyzed by transition metals makes it possible to dispense with the addition of additional anions which do not serve as ligands in such processes. The use of the nonaqueous ionic ligand liquids of the invention for preparing aldehydes from olefins or olefinically unsaturated compounds is the subject matter of a patent filed on the same day.

In the following examples, there are described several preferred embodiments to illustrate the invention. However, it is to be understood that the invention is not intended to be limited to the specific embodiments.

EXAMPLE 1

In a 2 liter three-necked flask with bottom outlet, 700 g of a sodium tri(sulfophenyl)phosphine solution of 453.9 mmol/kg of sodium tri(sulfophenyl)phosphine and 72.3 mmol/kg of sodium di(sulfophenyl)phenylphosphine were admixed at room temperature with a solution of 329.3 g of 1-amino-3-(di-n-octyl)-aminopropane (purity=95.6% by weight) in 493.9 g of toluene. While stirring, 516.4 g of sulfuric acid (20% strength by weight) were added over a period of 2 hours. After addition of sulfuric acid was complete, the mixture was stirred for another hour.

200 g of toluene were then added and the mixture was stirred for 10 minutes. After switching off the stirrer, the lower, aqueous phase comprising sodium hydrogen sulfate was separated off and the upper phase was washed with 500 g of toluene to remove remaining excess amine. This gave 1449.4 g of nonaqueous ionic ligand liquid.

EXAMPLE 2

In a 2 liter three-necked flask with bottom outlet, 1000 g of a sodium tri(sulfophenyl)phosphine solution of 453 mmol/kg of sodium tri(sulfophenyl)phosphine and 55 mmol/kg of sodium di(sulfophenyl)phenylphosphine were admixed at room temperature with a solution of 165.9 g of 1-amino-3-(di-i-nonyl)aminopropane (purity=97.75% by weight) in 497.8 g of toluene. While stirring, 248.5 g of sulfuric acid (20% strength by weight) were added over a period of 1.5 hours. After addition of sulfuric acid was complete, the mixture was stirred for another 1.5 hours.

After switching off the stirrer, the phases were allowed to settle for 10 minutes and three phases were obtained. After phase separation, 735.7 g of the middle phase which forms the nonaqueous ionic ligand liquid were obtained. The lower aqueous phase comprised sodium hydrogen sulfate while toluene formed the upper phase.

After addition of a transition metal or a transition metal compound, the nonaqueous ionic ligand liquids of the invention can be used as catalyst systems in chemical processes catalyzed by transition metals.

Various modifications of the products and process of the invention may be made without departing from the spirit or scope of thereof and it should be understood that the invention is intended to be limited only as defined in the appended claims.

What we claim is:

1. A nonaqueous ionic ligand liquid, insoluble in water and an organic solvent of the formula $(Q^{\oplus})_a\ A^{a-}$, wherein $Q^{\oplus}$ is a singly charged quaternary ammonium and/or phosphonium cation or the equivalent of a multiply charged ammonium and/or phosphonium cation and $A^{a-}$ is a triarylphosphine of the formula:

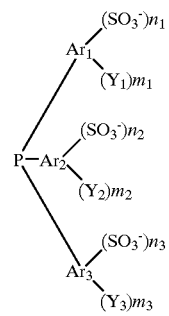

where $Ar_1$, $Ar_2$ and $Ar_3$ are individually aryl of 6 to 14 carbon atoms, $Y_1$, $Y_2$ and $Y_3$ are individually selected from the group consisting of alkyl of 1 to 4 carbon atoms, alkoxy of 1 to 4 carbon atoms, chlorine, bromine, hydroxyl, cyano, nitro and $-NR^1R^2$, where $R^1$ and $R^2$ are individually hydrogen or alkyl of 1 to 4 carbon atoms, $m_1$, $m_2$ and $m_3$ are individually integers from 0 to 5, $n_1$, $n_2$ and $n_3$ are individually integers from 0 to 3, where at least one of $n_1$, $n_2$ and $n_3$ is equal to or greater than 1, and a is $n_1+n_2+n_3$, and amines and/or phosphines derived from $Q^{\oplus}$ are present in an excess of up to 5 equivalents over the stoichiometrically required amount for the formation of $(Q^{\oplus})_a\ A^{a-}$ or alkali metal or alkaline earth metal salts of the triarylphosphines $A^{a-}$ are present in an excess of up to 5 equivalents over the stoichiometrically required amount for the formation of $(Q^\oplus)_a A^{a-}$.

2. A nonaqueous ionic ligand liquid of claim 1, wherein amines and/or phosphines derived from $Q^\oplus$ are present in an excess of up to 1 equivalent over the stoichiometrically required amount for the formation of $(Q^\oplus)_a A^{a-}$ or alkali metal and/or alkaline earth metal salts of the triarylphosphines $A^{a-}$ are present in an excess of up to 1 equivalent over the stoichiometrically required amount for the formation of $(Q^\oplus)_a A^{a-}$.

3. A nonaqueous ionic ligand liquid of claim 1 wherein $Q^\oplus$ is a quaternary ammonium and/or phosphonium cation of a formula:
selected from the group consisting of
$^\oplus NR^1R^2R^3R^4$, $^\oplus PR^1R^2R^3R^4$, $R^1R^{2\oplus}N=CR^3R^4$, $R^1R^{2\oplus}P=CR^3R^4$,

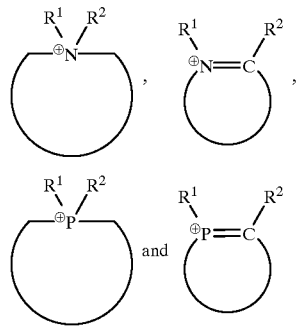

and where $R^1$, $R^2$, $R^3$ and $R^4$ are individually hydrogen, with the exception of $NH_4^+$, or hydrocarbon of 1 to 20 carbon atoms and in which the heterocycles have from 4 to 10 ring atoms.

4. A nonaqueous ionic ligand liquid of claim 1 wherein $Q^\oplus$ is a quaternary ammonium and/or phosphonium cation of a formula selected from the group consisting of $R^1R^{2\oplus}N=CR^3-X-R^3C=^\oplus NR^1R^2$ and $R^1R^{2\oplus}P=CR^3-X-R^3C=^\oplus PR^1R^2$, where $R^1$, $R^2$ and $R^3$ are individually hydrogen or hydrocarbon of 1 to 20 carbon atoms and X is alkylene or phenylene.

5. A nonaqueous ionic ligand liquid of claim 1 wherein $Q^\oplus$ is selected from the group consisting of N-butylpyridinium, N-ethylpyridinium, 1-n-butyl-3-methylimidazolium, diethylpyrazolium, 1-ethyl-3-methylimidazolium, pyridinium, triethylphenylammonium and tetrabutylphosphonium cation.

6. A nonaqueous ionic ligand liquid of claim 1 wherein $Q^\oplus$ is a quaternary ammonium and/or phosphonium cation of a formula selected from the group consisting of $R^1R^2R^3N^\oplus-(X)-N^\oplus R^4R^5R^6$ and $R^1R^2R^3P^\oplus-(X)-P^\oplus R^4R^5R^6$, where $R^1, R^2, R^3, R^4 R^5$ and $R^6$ are individually hydrogen or hydrocarbon of 1 to 20 carbon atoms and X is selected from the group consisting of 1,2-phenylene, 1,3-phenylene, 1,4-phenylene and $-(CHR^7)_b$, where $R^7$ is hydrogen or hydrocarbon of 1 to 5 carbon atoms, and b is an integer of 1 to 8.

7. A nonaqueous ionic ligand liquid of claim 6 wherein $R^1$, $R^2$, $R^3$, $R^4$, $R^5$ and $R^6$ are individually selected from the group consisting of hydrogen, n-butyl, n-pentyl, n-hexyl, n-heptyl, i-heptyl, n-octyl, i-octyl, n-nonyl, i-nonyl, n-decyl, i-decyl, n-undecyl, i-undecyl, n-dodecyl and i-dodecyl, $R^7$ is hydrogen, methyl or ethyl and b is 2, 3, 4, 5 or 6.

8. A nonaqueous ionic ligand liquid of claim 6 wherein $R^1$ and $R^2$ are individually selected from the group consisting of n-butyl, n-pentyl, n-hexyl, n-heptyl, i-heptyl, n-octyl, i-octyl, n-nonyl, i-nonyl, n-decyl, i-decyl, n-undecyl, i-undecyl, n-dodecyl and i-dodecyl, $R^3$, $R^4$, $R^5$ and $R^6$ are hydrogen, $R^7$ is hydrogen and b is 3.

9. A nonaqueous ionic ligand liquid of claim 1 wherein $Q^\oplus$ is tricyclodecane diammonium cation or N,N'-dimethyltricyclo-decanediammonium cation.

10. A process for preparing a nonaqueous ionic ligand liquid of claim 1 comprising reacting a solution of the amine and/or phosphine derived from $Q^\oplus$ with an acid and/or an alkylating agent in the presence of an aqueous solution of the alkali metal and/or alkaline earth metal salts of the triarylphosphines $A^{a-}$.

11. The process of claim 10 wherein 0.9 to 2.0 equivalents of acid and/or alkylating agent are used per equivalents of amine and/or phosphine.

12. The process of claim 10 wherein from 1 to 1.5 equivalents of acid and/or alkylating agent are used per equivalent of amine and/or phosphine.

13. The process of claim 10 wherein the acid used is selected from the group consisting of phosphoric acid, sulfuric acid, nitric acid, a phosphonic acid of 1 to 20 carbon atoms and a sulfonic acid of 1 to 20 carbon atoms.

14. The process of claim 10 wherein the acid used is an aqueous phosphoric acid solution or sulfuric acid solution.

15. The process of claim 10 wherein the alkylating agent used is a monoalkyl or dialkyl sulfate or a dialkyl carbonate of 1 to 41 carbon atoms or an alkyl halide of 1 to 10 carbon atoms.

16. The process of claim 10 wherein an aqueous sodium or potassium salt solution obtained from the sulfonation of triphenylphosphine is used.

17. The process of claim 10 wherein the solution is selected from the group consisting of benzene, toluene, o-xylene, m-xylene, p-xylene, mesitylene, n-heptane, n-octane, cyclohexane, tetrahydrofuran and 1,4-dioxane as solvent for the amine and/or phosphine derived from $Q^\oplus$.

18. The process of claim 10 carried out at a temperature of from 0 to 60° C.

19. In a chemical process catalyzed by the transition metals, the improvement comprising using as the catalyst, a nonaqueous ionic ligand liquid of claim 1.

20. The process of claim 19 wherein the catalyst constituent is used in a two-phase process.

* * * * *